United States Patent [19]

Dunkel

[11] Patent Number: 4,647,780

[45] Date of Patent: Mar. 3, 1987

[54] APPARATUS FOR MEASURING SMOKE DENSITY

[75] Inventor: Kelvin Dunkel, Peterborough, United Kingdom

[73] Assignee: Perkins Engines Group Limited, London, England

[21] Appl. No.: 659,149

[22] Filed: Oct. 9, 1984

[51] Int. Cl.$^4$ ............................................. G01N 21/59
[52] U.S. Cl. .................................. 250/573; 250/564; 356/438
[58] Field of Search ............ 250/573, 564, 574, 214 C, 250/238; 356/437, 438, 439, 335; 350/584; 340/630

[56] References Cited

U.S. PATENT DOCUMENTS

| | | | |
|---|---|---|---|
| 3,847,487 | 11/1974 | Ball | 356/438 |
| 3,861,198 | 1/1975 | Shea | 350/584 |
| 3,908,167 | 9/1975 | Hulls | 356/438 |
| 4,038,555 | 7/1977 | Freeman | 250/238 |
| 4,277,131 | 7/1981 | Hart | 356/439 |
| 4,413,911 | 11/1983 | Rice | 350/584 |
| 4,544,273 | 10/1985 | Berndt | 356/439 |

*Primary Examiner*—Edward P. Westin
*Attorney, Agent, or Firm*—Robert L. Farris

[57] ABSTRACT

Smoke density measuring apparatus comprising a duct (1) through which the smoke passes, a light source (4) and a photodetector (6) located on opposite sides of the duct adjacent openings (2,3) in the side walls of the duct so that the source (4) directs a beam of light across the duct through the openings to the photodetector (6), a gas supply (10) associated with the openings (2,3) in the side walls of the duct so that gas flows through each opening into the duct, gas flow control valve (13) for varying the rate of flow of gas through said openings, sensor (17) for monitoring the rate of flow of smoke through the duct, and a control circuit (FIG. 4) for controlling the gas flow control valve (13) in a manner dependent on operation of the sensor (17) so that the rate of flow of gas through the openings is reduced when the rate of flow of smoke falls below a predetermined value. The control circuit (FIG. 4) operates to reduce the flow of gas from a first to a second predetermined flow rate when the rate of flow of smoke falls below the predetermined value. The smoke flow rate sensor (17) comprises a smoke temperature sensor. Smoke density assessing circuitry has inputs from the photodetector (6) and temperature sensor (17) and includes correction device (20) that operates to multiply the smoke density measurement by a correction factor that increases with smoke temperature. The correction factor takes account of changes of gas density with temperature, the occurrence of smoke particle agglomeration with decreasing exhaust gas temperature, and changes of effective optical path length.

9 Claims, 6 Drawing Figures

APPARATUS FOR MEASURING SMOKE DENSITY

BACKGROUND OF THE INVENTION

This invention relates to apparatus for measuring smoke density using a beam of light through which the smoke passes to attenuate the intensity of the transmitted light depending on the smoke density.

Known smoke density measuring apparatus of the aforesaid kind comprises a duct through which the smoke passes, a light source that directs a collimated beam of light across the duct to a photodetector on the opposite side, both the light source and the photodetector being housed in chambers that open into the side walls of the duct and which are supplied with air under pressure so that there is a constant flow of air into the duct to prevent the entry of smoke that might otherwise deposit smoke particles within the chambers and produce measuring errors. As a result of the air flow into the duct, the flow of smoke is modified and produces a reduction in the width of the column of smoke across the light path. The effective optical path length is therefore less than the actual duct width and is found to vary with the rate of flow of the smoke column through the duct. Therefore, in order to avoid significant measuring errors the smoke flow rate is maintained constant or at least above a minimum level below which a reduction in the flow rate has a progressively more significant effect. The problem with this restriction is that the same apparatus cannot then be used for a wide variation of smoke flow rates such as are met when measuring smoke in the exhaust of different size engines operating at different speeds.

Another characteristic of the known smoke density measuring apparatus is that at lower smoke temperatures agglomeration of the smoke particles can occur and produce lower smoke density measurements. In order to avoid such effects the known apparatus is restricted to measurements above a pre-determined minimum smoke temperature, and once again the scope of use of the apparatus is limited, at least as far as the measurement of engine exhaust smoke is concerned.

An object of the present invention is to provide smoke density measuring apparatus in which the above limitations are reduced or overcome.

SUMMARY OF THE INVENTION

According to one aspect, the invention consists in smoke density measuring apparatus comprising a duct through which the smoke passes, a light source and a photodetector located on opposite sides of the duct adjacent openings in the side walls of the duct so that the source directs a beam of light across the duct through the openings to the photodetector, a gas supply associated with said openings in the side walls of the duct so that gas flows through each opening into the duct, gas flow control means for varying the rate of flow of gas through said openings, sensor means for monitoring the rate of flow of smoke through the duct, and control means for controlling said gas flow control means in a manner dependent on operation of the sensor means so that the rate of flow of gas through said openings is reduced when the rate of flow of smoke falls below a predetermined value.

Preferably, the control means operates to reduce the flow of gas from a first to a second predetermined flow rate when the rate of flow of smoke falls below said predetermined value. Each flow rate is selected as an optimum value to produce an overall minimum acceptable measurement variation with flow rate.

According to another aspect, the invention consists in smoke density measuring apparatus comprising a duct through which the smoke passes, a light source and a photodetector located on opposite sides of the duct so that the source directs a beam of light across the duct to the photodetector, a temperature sensor to sense the temperature of the smoke flowing through the duct, and smoke density assessing means having inputs from the photodetector and temperature sensor and including correction means that operates to multiply the smoke density measurement by a correction factor that increases with smoke temperature.

The correction factor preferably takes account of changes of gas density with temperature, the occurrence of smoke particle agglomeration with decreasing exhaust gas temperature, and changes of effective optical path length. Preferably, this factor is determined empirically and is taken as a linear function.

BRIEF DESCRIPTION OF THE DRAWINGS

The invention will now be described by way of example with reference to the accompanying drawings in which.

DESCRIPTION OF THE PREFERRED EMBODIMENTS

Figure 1:
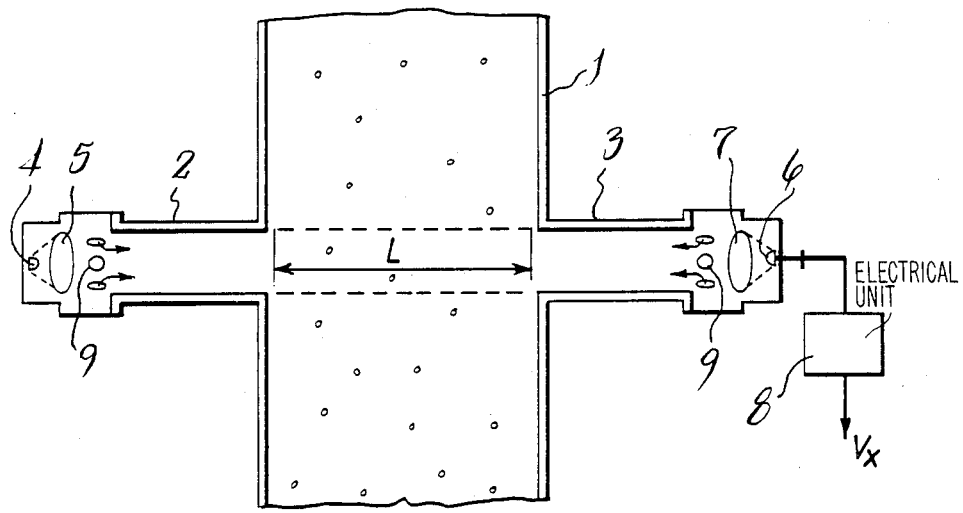
FIG. 1 is a schematic section through known exhaust gas smoke density measuring apparatus employing a light beam.

The illustrated smoke density measuring apparatus comprises a duct 1 that is adapted to be connected to a diesel engine exhaust so that the exhaust gases flow through it. Two tubes 2,3 open into the side wall of duct 1 at diametrically opposite points thereof and are axially aligned. A light source in the form of a light emitting diode 4 is mounted at the end of one tube 2, and light from the source passes through a lens system 5 to produce a collimated light beam that is directed across the duct into the tube 3. A light photodetector 6 is mounted at the end of the tube 3 and a lens 7 focuses the collimated beam of light onto the photodetector 6 to produce an electrical output signal proportional to the intensity of the light transmitted through the exhaust gases and which is conditioned in an electrical unit 8 to produce an output signal Vx equal to the smoke density of the exhaust gases.

Figure 2:
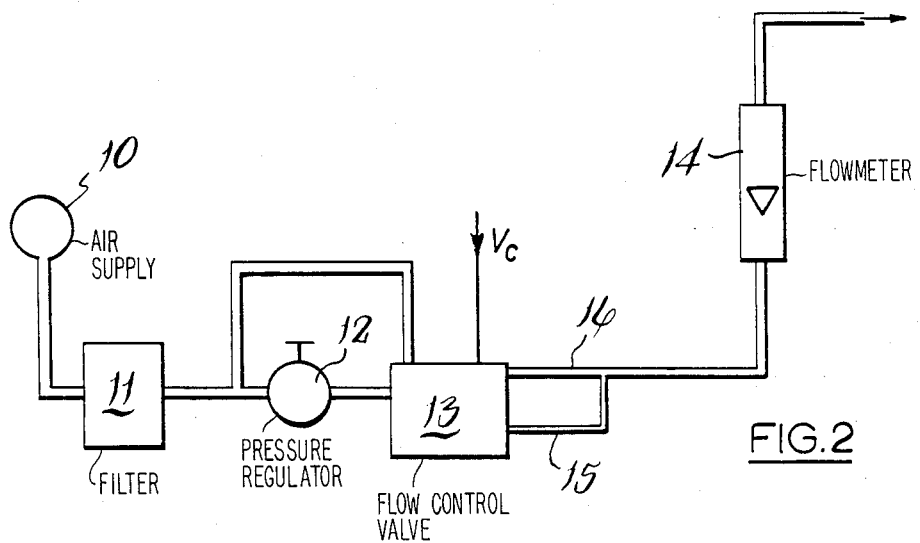
FIG. 2 is a schematic diagram showing air flow control apparatus according to the invention.

A compressed air supply is connected to the housing of the light source 4 and the photodetector 6 through inlet apertures 9 and serves to produce a constant flow of air through each tube 2 and 3 into the duct 1 so as to prevent exhaust gases from entering said housings and contaminating the light source and photodetector. The effective optical path length L of the light beam through the exhaust gases will vary with the rate of flow of the exhaust gases and the rate of flow of the air through tubes 3 and 4. Thus, in order to maintain the effective optical path length substantially constant for standardised light intensity readings, the air flow is reduced with the exhaust gas flow using the apparatus illustrated in FIG. 2.

Figure 3:
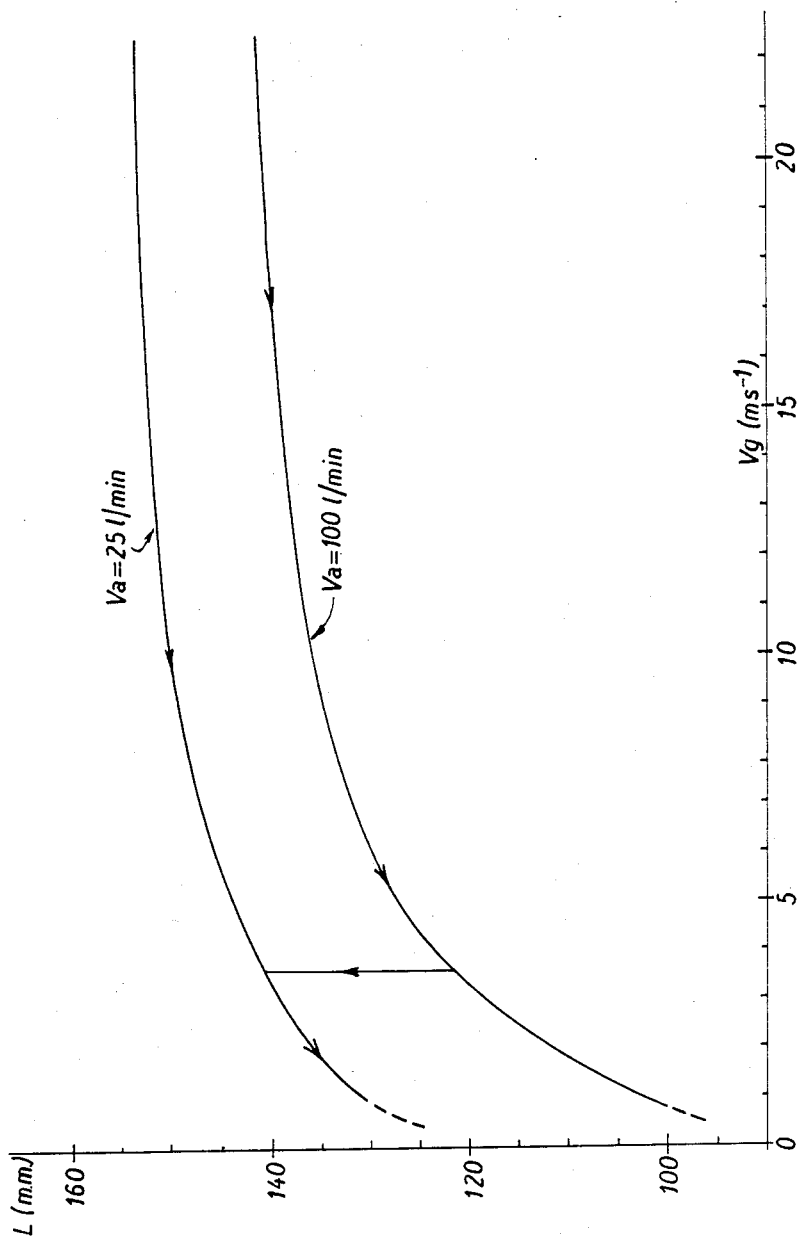
FIG. 3 shows how effective optical path length L varies with exhaust gas flow rate in the apparatus of FIG. 1.

The compressed air supply 10 is connected to the light source and photodetector housings via a filter 11, a pressure regulator 12, a flow control valve 13, and flowmeter 14. The valve 13 is a two-position solenoid-operated valve that switches the input air supply between either of two outlet connections 15 and 16 that are connected in parallel to the flowmeter 14. Outlet connection 15 has a smaller bore diameter than outlet connection 16 so that the valve 13 produces either a high air flow rate through connection 16 or a low air flow rate through connection 15. An electrical control signal Vc serves to operate the valve 13 so as to switch from the high to the low air flow rates when the exhaust gas flow rate falls below a predetermined flow rate. FIG. 3 illustrates how the effective optical path length L varies with the exhaust gas flow rate Vg for the two different air flow rates Va, and how changing from one to the other helps produce a more constant effective optical path length overall.

Typically, apparatus for measuring exhaust smoke in a range of different capacity diesel engines, has a duct 1 of 6-inch diameter, a high air flow rate of 100 liters/minute, a low air flow rate of 25 liters/minute and switches from the high to the low air flow rate at an exhaust flow rate Vg of 4 meters/second.

Figure 4:
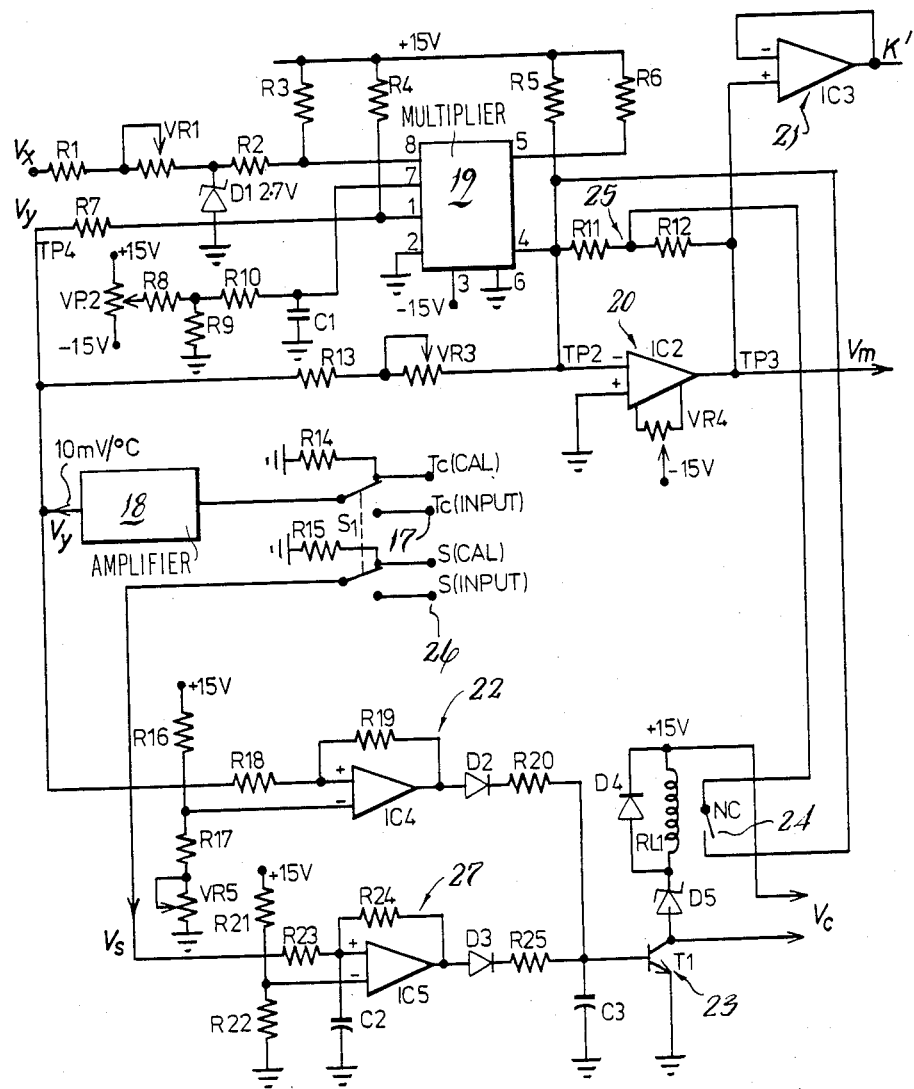
FIG. 4 shows control circuitry according to the invention for controlling the air flow control apparatus of FIG. 2.

The electrical control circuitry that produces the electrical control signal for valve 13 and that processes the signal Vx from unit 8 to give a smoke measurement is illustrated in FIG. 4. A thermocouple 17 is provided in the duct 1 to measure the exhaust gas temperature and produces a signal that is amplified in an amplifier 18 to produce a corresponding temperature signal Vy. The signals Vx and Vy are fed to an analogue multiplier 19 that is set so as to provide gain modulation of the light intensity signal Vx as a linear function of the temperature signal Vy, thereby correcting for the aforesaid effect of reducing smoke density measurement with increasing exhaust gas temperature. The resulting output current from amplifier 19 is fed to an operational amplifier 20 which converts it to a corresponding voltage signal Vm suitable for operating a recorder unit via an amplifier 21 and a display meter (not shown) to display the smoke density measurement.

Based on the fact that the exhaust gas temperature varies with the exhaust gas flow rate, the temperature signal Vy is used to determine when the exhaust gas flow rate falls below said predetermined flow rate, the valve 13 then being operated. Typically, the predetermined exhaust gas flow rate of 4 meters/second is found to correspond to an exhaust gas temperature of 350 degrees Centigrade, and thus the signal Vy is monitored and compared with said corresponding reference temperature of 350 degrees Centigrade in a comparator amplifier 22. When the exhaust temperature falls below the reference temperature, the amplifier 22 produces an output signal that operates a transistor switch 23 and thereby produces the control signal Vc to de-engerise the valve 13 and switch it from the high to the low air flow settings. Conversely, as the exhaust temperature rises above the reference temperature, the amplifier 22 and transistor switch 23 operate to energise the valve 13 and switch it from the low to the high air flow settings. In fact, the comparator amplifier 22 has a hysteresis characteristic so that it only responds to operate switch 23 and energise valve 13 at a temperature above said reference temperature (e.g. 360 degrees Centigrade) so as to avoid switching oscillations at the reference temperature.

Operation of switch 23 to energise valve 13 also serves to operate a reed relay 24 that shorts out one of the feedback resistors 25 in amplifier 20 and so reduces its gain by a predetermined factor, typically 1.17, when the exhaust gas temperature falls below the said reference temperature of 350 degrees Centigrade. This compensates for the increase in smoke density measurement (typically 17%) when the purge flow Va switches from 100 liters/minute to 25 liters/minute.

Figure 5:
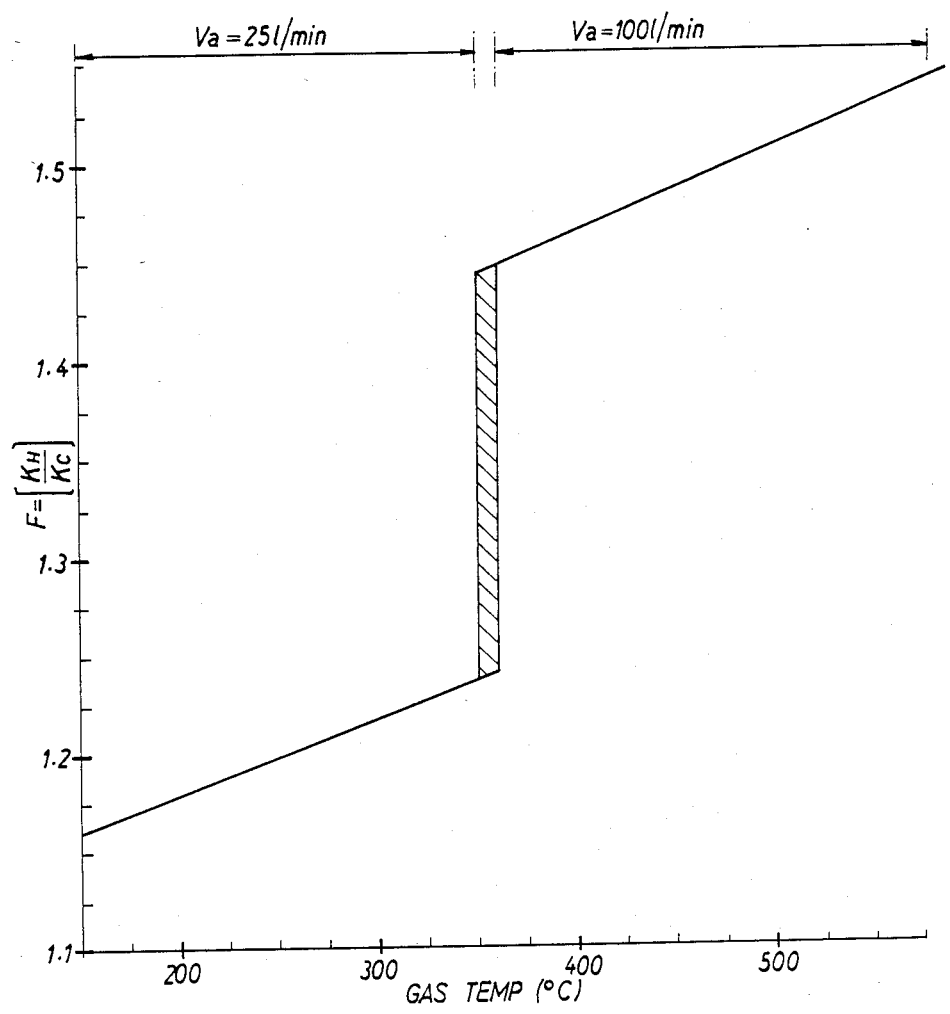
FIG. 5 shows the correction factor F used as the gain characteristic in the control circuitry of FIG. 4.
Figure 6:
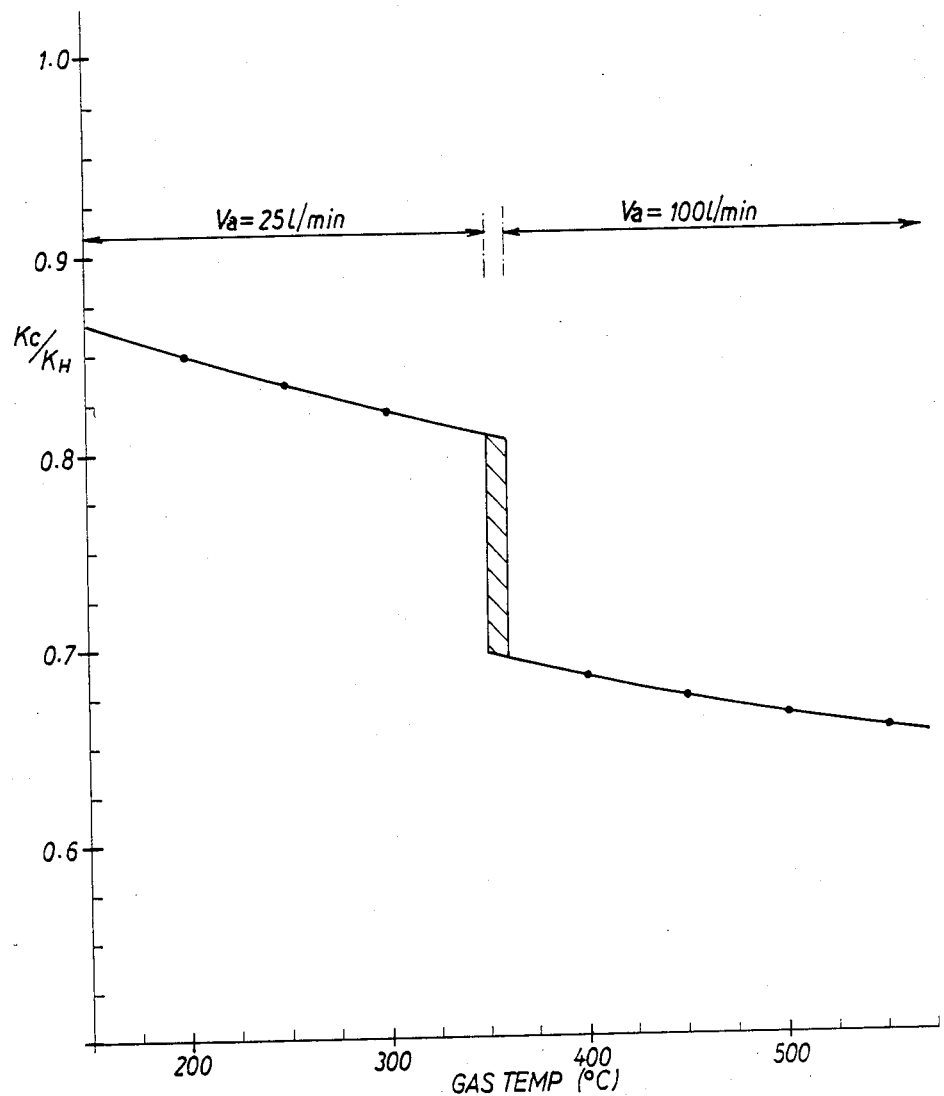
FIG. 6 shows the ratio of equivalent smoke density measurements used to determine the correction factor F in FIG. 5.

The overall gain characteristic of amplifiers 19 and 20 which is applied as a correction factor F to the smoke density signal Vx is illustrated in FIG. 5. This is predetermined from a comparison of equivalent smoke density measurements K using the illustrated apparatus (Kc) and conventional Hartridge smoke measuring apparatus set for readings at 100 degrees Centigrade (KH). FIG. 6 shows the ratio of such comparative measurements KC/KH over the temperature range 150 to 550 degrees Centigrade for gases from a lagged diesel engine exhaust. It will be appreciated that the correction factor F is the inverse of this ratio, i.e. KH/KC, and is shown as a linear function either side of the reference exhaust gas temperature 350 degrees Centigrade in FIG. 5. The change in gain of amplifier 20 at the switch-over temperatures of 350 and 360 degrees Centigrade is a factor of 1.17 corresponding to a change in the correction factor F between 1.24 and 1.44.

The electrical control circuitry of FIG. 4 also includes a sensor 26 to sense the speed of the diesel engine whose exhaust gases are being tested, and this produces an engine speed signal Vs that is fed to a comparator amplifier 27 that compares the signal Vs with a predetermined engine speed and produces an output signal at speeds below 2000 r.p.m. to operate the switch 23 and causes valve 10 to switch from the high to the low air flow rate. Amplifier 27 has a hysteresis characteristic like amplifier 22, and the operating limits are 2000 and 2050 r.p.m. to avoid switching oscillations.

This arrangement ensures that even if the exhaust temperature is below the reference temperature, the valve 13 will be operated to switch to high air flow rate if the engine speed rises above said reference speed. This operating condition reduces the possibility of deposition of smoke particles in the light source and photodetector housings in the event of high exhaust back pressure and low exhaust gas temperatures, for example in six and eight cylinder diesel engines run near rated speed (2,200 r.p.m. and above) and light loads.

I claim:

1. Smoke density measuring apparatus comprising a duct formed by side walls and through which the smoke passes, a first opening in a side wall of the duct, a second opening in a side wall of the duct opposite the side wall with the first opening, a light source mounted outside the duct and adjacent the first opening so that the light source directs a beam of light through the first opening, across the duct and through the second opening, a photodetector mounted outside the duct and adjacent the second opening to receive light from the light source, said photodetector producing an output signal proportional to the smoke density, a gas supply connected to said openings in the side walls of the duct so that the gas flows through each opening into the duct, gas flow control valve means for varying the rate of flow of gas through said openings, sensor means for monitoring the rate of flow of smoke through the duct, and control means connected to said sensor means for controlliong said gas flow control valve means in a manner dependent on operation of the sensor means so that the rate of flow of gas through said openings is reduced when the rate of flow of smoke falls below a predetermined value.

2. Apparatus as claimed in claim 1 in which the gas flow control means has two predetermined control settings corresponding to higher and lower gas flow rates, and is controlled by said control means so as to be switched from the higher to the lower flow rate setting when the rate of flow of smoke falls below said predetermined value.

3. Apparatus as claimed in claim 1 in which said sensor means comprises a temperature sensor that is located in said duct so as to be responsive to the temperature of smoke, said predetermined value of the rate of flow of smoke corresponding to a reference temperature.

4. Apparatus as claimed in claim 3 which includes smoke density assessing means having electrical inputs from the photodetector and from the temperature sensor and correction means that operates to multiply the smoke density measurement by a correction factor that increases with smoke density.

5. Apparatus as claimed in claim 4 in which the correction factor comprises a substantially linear function with temperature of the smoke.

6. Apparatus as claimed in claim 5 in which the correction factor includes a discontinuity at a value of the temperature signal corresponding to said reference temperature.

7. Apparatus as claimed in claim 1 in which the control means is such that the rate of flow of gas through said openings is increased when the rate of flow of smoke rises above a predetermined value which is higher than said predetermined value at which the rate of flow of gas is reduced, the change of rate of flow of gas being the same in both instances but the different predetermined change values giving a hysteresis characteristic.

8. Apparatus as claimed in claim 1 which includes speed sensor means for sensing the speed of an engine producing exhaust smoke to be measured, the sensor producing a corresponding engine speed signal which is fed to said control means, and the control means operating to reduce the rate of gas flow through said openings when the engine speed is below a predetermined reference engine speed but maintaining the rate of gas flow when the engine speed is above a predetermined reference engine speed irrespective of the rate of flow of smoke.

9. Smoke density measuring apparatus comprising a duct through which the smoke passes, a light source and a photodetector located on opposite sides of the duct so that the source directs a beam of light across the duct to the photodetector, a temperature sensor to sense the temperature of the smoke flowing through the duct, and smoke density assessing means having inputs from the photodetector and temperature sensor and including correction means that operates to multiply the smoke density measurement by a correction factor that increases with smoke temperature.

* * * * *